United States Patent [19]

Holtkamp

[11] Plant 5,024

[45] Apr. 5, 1983

[54] AFRICAN VIOLET PLANT

[76] Inventor: Reinhold Holtkamp, Werther Strasse 112, 4294 Isselburg, Fed. Rep. of Germany

[21] Appl. No.: 300,633

[22] Filed: Sep. 9, 1981

[51] Int. Cl.[3] ..... A01H 5/00
[52] U.S. Cl. ..... Plt./69
[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new cultivar of African violet referred to by the cultivar name Crater Lake having semi-double to double blossoms with up to ten petals per blossom, purple-blue in color. The plant is a vigorous grower, producing 7-11 strong, sturdy, tilted flower stems each of which carries 11 or more flowers. The variety is further characterized by its shiny and slightly hairy leaves and by its dark brown flower stems and peduncles.

1 Drawing Figure

The present invention comprises a new and distinct cultivar of African violet plant, botanically known as *Saintpaulia ionantha,* and hereinafter referred to by the cultivar name of Crater Lake.

The new cultivar was referred to during the breeding and selection process by the designation d 210/0, and is a product of a planned breeding program. The basic objective of the breeding program was to create a new African violet cultivar having a compact growth habit, tight and profuse corolla on sturdy stems, and semi-double blossoms.

The new cultivar was originated from a cross made in a controlled breeding program in Isselburg, West Germany. The female, or seed parent was a cultivar designated 26 ANT blue semi-double. The male, or pollen parent was a cultivar designated 2 229/11 pin star semi-double.

The new cultivar Crater Lake was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Crater Lake has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Crater Lake, which in combination distinguish this African violet as a new and distinct cultivar:

1. Seven to eleven strong, sturdy tilted flower stems.
2. Eleven or more flowers per stem.
3. Short hairy peduncles.
4. Dark brown flower stems and peduncles.
5. Semi-double to double flowers with up to 10 petals purple-blue in color.
6. Shiny and slightly hairy leaves.
7. Vigorous grower.

8. Saleable plant with compact flower heat (corolla) within 8-9 weeks.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Crater Lake.

Parentage:

*Male parent.*—2 229/11 pink star semi-double.

*Female parent.*—26 ANT blue semi-double.

Propagation: The new cultivar holds its distinguishing characteristics through successive propagations by leaf cuttings and by division of shoots.

Plant: From 6 cm. to 8 cm. tall when grown in pots, and approximately 23-25 cm. in diameter when fully grown.

Leaves:

*General form.*—Oval.

*Diameter.*—50-60 mm.

*Texture.*—Leathery, slightly hairy.

*Aspect.*—Shiny.

*Veins.*—Upperside visible.

*Color (upperside).*—HCC ivy green 0001060/3.

*Color (underside).*—Brownish purple.

*Petiole.*—Young petiole purplish brown, hairy; brownish green.

Flowers:

*Buds.*—Ball-shaped; 8-10 mm. just before opening; 9-10 per stem.

*Sepals.*—Color: Dark brown. Calyx: funneled. Aspect: spear-shaped, hairy. Peduncle: Short, sturdy, dark brown.

Individual flowers:

*Size.*—Up to 45 mm.

*Color.*—Upperside: Victoria violet 738. Underside: Methyl violet 39.

*Borne.*—Flower stem carries 9-11 flowers on short strong peduncles; basically double, but a few flowers appear semi-double.

*Shape.*—Conventional, 2 upper and 3 larger lower petals.

*Flowering time.*—First flowers appear 6–7 weeks after potting; after 8–10 weeks full flowering saleable plant.

Reproductive organs:

*Stamens.*—2 anthers, composed of 2 cells, with seed capsule pushed slightly through.

*Anthers.*—HCC Dresden yellow 64/3.

*Filaments.*—4 mm. long; light green with partly blueish purple.

*Styles.*—7 mm.; aconite violet 937/3; base of ovary light green and hairy.

*Pollen color.*—HCC Dresden yellow 64.

Roots: White when young and active; greenish brown when older; normally developed.

Disease resistance: Good as experienced to date.

General observations: Crater Lake is a very interesting variety having semi-double to double blossoms. The flower stems, which are strong and sturdy, are slightly tilted and carry nine to eleven or more individual flowers. Its deep purplish-blue blossoms, whose centers appear darker with well-visible anther cells, are long-lasting and non-dropping.

I claim:

1. A new and distinct cultivar of African violet known by the cultivar name Crater Lake and particularly characterized by the combined features of semi-double to double flowers with up to ten petals purple-blue in color; seven–eleven strong, sturdy tilted flower stems, with each carrying eleven or more flowers; short hairy peduncles; dark brown flower stems and peduncles; shiny and slightly hairy leaves, vigorous growth habit, and by its ability to produce a saleable plant with a compact flower head within 8–9 weeks after potting.

* * * * *

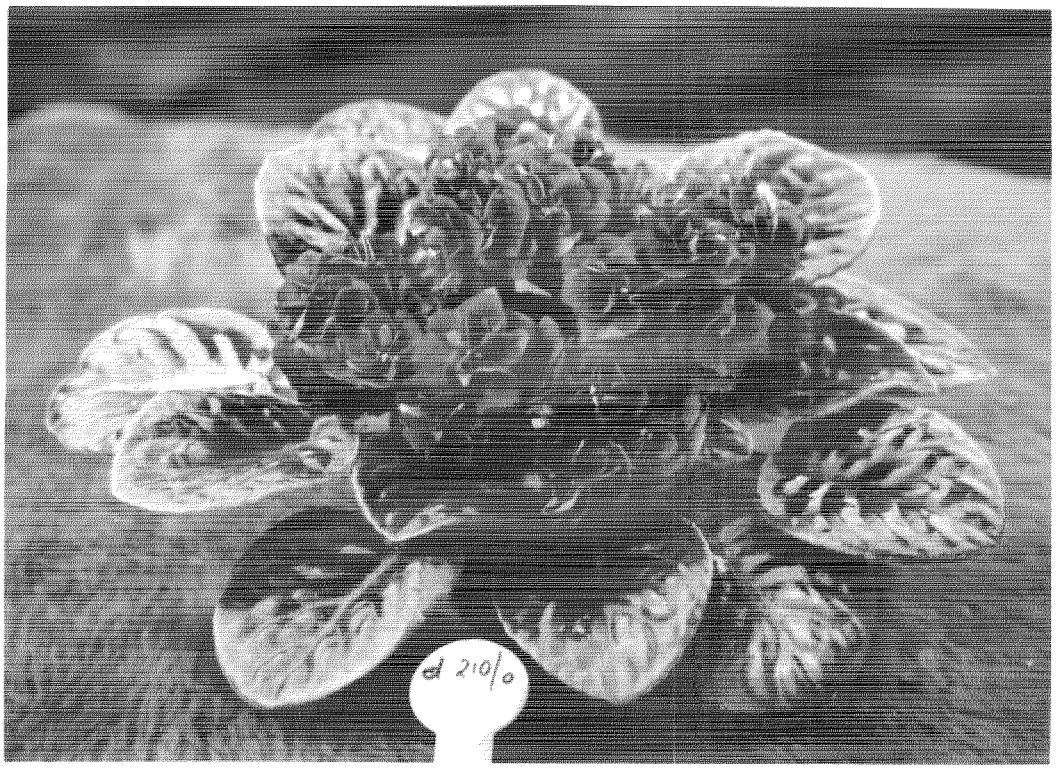
d 210/0